United States Patent [19]

Paul

[11] Patent Number: 5,556,030
[45] Date of Patent: * Sep. 17, 1996

[54] AIR FRESHENER AND/OR DEODORIZER DISPENSING SYSTEM

[76] Inventor: Leonard Paul, 13 Stuart Dr., Bloomfield, Conn. 06002

[*] Notice: The term of this patent shall not extend beyond the expiration date of Pat. No. 5,373,303.

[21] Appl. No.: 333,027

[22] Filed: Nov. 1, 1994

Related U.S. Application Data

[63] Continuation-in-part of Ser. No. 163,338, Dec. 6, 1993, Pat. No. 5,372,303.

[51] Int. Cl.$^6$ .................................................. A61L 9/12
[52] U.S. Cl. .................................................. 239/56; 239/58
[58] Field of Search .............................. 239/34, 44, 49, 239/51.5, 53–56, 58, 60

[56] References Cited

U.S. PATENT DOCUMENTS

| | | | |
|---|---|---|---|
| 2,615,754 | 10/1952 | Lindenberg | 239/56 |
| 2,626,833 | 1/1953 | Valentine | 239/56 |
| 3,985,298 | 10/1976 | Nichols | 239/54 |
| 4,283,011 | 8/1981 | Spector | 239/36 |
| 4,356,969 | 11/1982 | Obermayer et al. | 239/60 X |
| 4,517,308 | 5/1985 | Ehlenz et al. | 502/401 |
| 4,529,125 | 7/1985 | Sullivan | 239/56 |
| 4,596,844 | 9/1987 | Spector | 428/46 |
| 4,634,614 | 1/1987 | Holzner | 428/35 |
| 4,712,737 | 12/1987 | Hecking | 239/58 |
| 4,808,466 | 2/1989 | Kotani et al. | 428/254 |
| 4,814,212 | 3/1989 | Spector | 428/14 |
| 4,900,765 | 2/1990 | Murabayashi et al. | 523/122 |
| 4,923,119 | 5/1990 | Yamamoto et al. | 239/55 |
| 4,998,671 | 3/1991 | Leifheit | 239/56 |
| 5,046,604 | 9/1991 | Forhetz et al. | 206/0.5 |
| 5,071,704 | 12/1991 | Fischel-Ghodsian | 428/354 |
| 5,164,178 | 11/1992 | Muysson | 424/6.4 |
| 5,395,047 | 3/1995 | Pendergrass, Jr. | 239/34 X |

FOREIGN PATENT DOCUMENTS

| | | | |
|---|---|---|---|
| 1191863 | 4/1989 | Japan | 239/56 |
| 2161383 | 1/1986 | United Kingdom | 239/56 |

*Primary Examiner*—Lesley D. Morris
*Attorney, Agent, or Firm*—Melvin I. Stoltz

[57] ABSTRACT

By providing a unique fragrance composition which incorporates a fixative for controlling the rate of dispersion of the fragrance and associating the fragrance composition with cotton-based wicking member which is securely sealed in a flexible container formed from a multi-layered sheet material, a unique and highly advantageous air freshener and/or deodorizer dispensing system is attained. In the preferred embodiment, the multi-layered flexible container is constructed for cooperating association with all conventional heating systems which enables the temperature of the fragrance composition to be raised, causing its dispersion throughout the desired area to be substantially enhanced. In addition, in the preferred embodiment, the dispensing system of this invention employs a small, compact and flexibly moldable container or housing which enables the dispensing system to be easily positioned in any desired location, regardless of the size constraints imposed thereon.

17 Claims, 2 Drawing Sheets

AIR FRESHENER AND/OR DEODORIZER DISPENSING SYSTEM

This application is a continuation-in-part application of U.S. Ser. No. 08/163,338, filed Dec. 6, 1993 now U.S. Pat. No. 5,372,303.

TECHNICAL FIELD

This invention relates to air fresheners and/or deodorizers and, more particularly, to an integrated system for containing and dispensing the desired air freshening/deodorizing fragrance over extended time periods.

BACKGROUND ART

Air freshening or deodorizing has long been sought by consumers, in both residential and commercial environments. Due to the wide variety of odors which are generated, the desire to reduce or eliminate offensive odors has long existed along with the desire to provide a long-lasting pleasing odor.

In an attempt to meet the demand for air fresheners or deodorizers, numerous products have been developed and are presently available in the marketplace. In general, these prior art products are sold as solids, liquids, or aerosol sprays to provide the desired air freshening or deodorizing effect. Typically, these prior art products are used to eliminate, chemically change, or mask an existing odor. In addition, these products typically work by absorbing odorous molecules, dissolving or emulsifying such molecules, or killing bacteria that causes the offensive odor.

Although substantial effort has been expended in providing various delivery systems for establishing a pleasant odor in areas or environments in which offensive odors continuously exist, no fully satisfactory delivery system has been attained which is capable of providing long-term deodorizing or air freshening. In particular, such prior art systems as spray deodorants are capable of providing only temporary relief in freshening the air or eliminating the undesirable odors. Once the product has been sprayed into the air, the odor-changing spray quickly dissipates, providing only temporary or transitory relief. This limited benefit is particularly true in environments where heating or cooling is provided by forced air flow, since the air flow further increases air turbulence, causing the air freshening spray to dissipate more rapidly.

Similar short term beneficial effects are also attained with the liquid and solid air freshening products which are capable of only providing limited distribution of the deodorizer or air freshener and often become depleted of any beneficial effect over a short duration. Consequently, these products have only been capable of realizing limited acceptance and use.

Prior art systems typically range from simple dispensers containing the air freshening material to more complex, delivery systems constructed for decorative or designer effects. Unfortunately, such decorative effects cause such products to be substantially more expensive, with the ability of these products to deliver long-term continuous air freshening or deodorizing not being enhanced.

One prior art system employs a multi-layered flexible package for use in association with vacuum cleaners in order to provide air freshening or deodorizing during the vacuuming operation. However, these products are typically not capable of being employed in other environments and are unable to provide long-lasting, continuous, dependable air freshening or deodorizing due to the use of sponge material as the fragrance carrier. As a result, these prior art products lacked versatility and broad-based usability.

Another prior art system attempts to achieve greater fragrance distribution by using electricity to heat the dispenser. Although greater fragrance distribution is attained over solid, non-heated dispensers, these prior art systems are extremely expensive and provide only a very limited, moderate improvement.

Therefore, it is a principal object of the present invention to provide a fully integrated, air freshener and/or deodorizer dispensing system which provides a highly concentrated, readily dispersible air freshening/deodorizing composition which is capable of providing long-term, delivery of the desired fragrance.

Another object of the present invention is to provide an air freshener/deodorizer dispensing system having the characteristic features described above which provides a fully integrated, leak-free container system with a fragrance holding and dispersing system which assures continuous, complete and controlled dispersion of the fragrance only when desired by the user.

Another object of the present invention is to provide an air freshener/deodorizer dispensing system having the characteristic features described above which is capable of providing an easily employable, variable opening system for enabling the user to control the amount of fragrance being dispersed.

Another object of the present invention is to provide an air freshener/deodorizer dispensing system having the characteristic features described above which is capable of being easily positioned in a wide variety of locations, previously unattainable, due to the overall construction of the dispensing system of the present invention.

A further object of the present invention is to provide an air freshener/deodorizer dispensing system having the characteristic features described above which is capable of being easily employed in both residential and commercial establishments for providing long-term air freshening and/or deodorizing throughout the entire building or zone within which the system is employed.

Another object of the present invention is to provide an air freshener/deodorizer dispensing system having the characteristic features described above which is easily employed in air conditioning and heating ducts or other heat delivering systems.

Another object of the present invention is to provide an air freshener/deodorizer dispensing system having the characteristic features described above which is safe for use with children as well as constructed in a dispensing system which virtually eliminates any possibility of unwanted use or contact by children.

Another object of the present invention is to provide an air freshener/deodorizer dispensing system having the characteristic features described above which is able to cooperate with all conventional heating and cooling systems to circulate the desired fragrance without requiring mounted engagement with electrical outlets.

Other and more specific objects will be in part be obvious and will in part appear hereinafter.

SUMMARY OF THE INVENTION

The present invention overcomes all of the difficulties and drawbacks of prior art systems by providing a unique air freshener and/or deodorizer dispensing system which comprises a highly concentrated, oil-based solution of the desired fragrance associated with a highly or super absorbent wicking member which is contained in a small, compact, multi-layered flexible package. The multi-layered, flexible housing or container employed as part of the dispensing system of the present invention is completely flexible and moldable into virtually any desired configuration. In this way, the dispensing system is capable of being positioned in virtually any desired location, regardless of size constraints.

Another feature of the present invention is the attainment of an air freshener/deodorizer dispensing system which is completely sealed prior to actual use and is constructed with a housing or container which is virtually impervious to the air freshening/deodorizing composition incorporated therein. Consequently, prior to user-initiated, controlled opening of the dispensing system, the contents are maintained completely sealed within the container, incapable of being released until desired. As a result, each package of the dispensing system is capable of being stored for virtually any desired period of time with assurance that the product will possess all of the desired air freshening/deodorizing capabilities whenever the package is opened for use.

Another feature of the present invention is the construction of the air freshener/deodorizer dispensing system which enables the user to control the size of the portal or opening in the housing through which the fragrance passes. In this way, depending upon the amount of air freshening or deodorizing desired by the user, the housing or container can be opened minimally or completely in order to regulate the rate at which the fragrance is dispensed from the housing or container. In this way, any desired application can be easily accommodated.

In the preferred embodiment, the flexible housing or container is constructed with a notch zone formed in a sealed zone of the housing to enable the user to open the dispensing system by advancing the notch into the pouch area within which the fragrance and wicking means are contained. By controlling the area being opened, the desired dispensing portal can be quickly and easily achieved.

If desired, other constructions can be employed in order to control the size of the dispensing zone. One such alternate construction, which has been found to be highly effective, is the incorporation of a plurality of apertures formed along one edge of the interior pouch or holding zone, in association with an overlying, removable, sealing strip which seals the apertures, maintaining the air freshening/deodorizing composition completely potent until use is desired. Whenever needed, the user merely removes all, or a portion of the sealing strip, exposing the desired number of apertures needed for the particular application. In this way, an alternate construction for completely controlling the amount of fragrance being dispensed is attained.

In the preferred embodiment of the present invention, the wicking means comprises cotton material positioned in the holding zone or pouch in direct contact with the air freshening/deodorizing composition. Typically, the air freshening/deodorizing composition is fully absorbed throughout the wicking material, with any remaining supply of air freshening/deodorizing composition being pooled in one area of the holding zone with the wicking means in contact therewith. In this way, when the dispensing system is opened and a portion of the air freshening/deodorizing composition is expelled through the dispensing zone, the wicking material is continuously supplied with additional air freshening/ deodorizing composition until all of the material has been absorbed into the wicking material and dispensed.

The cotton wicking means may be constructed with the cotton material either in a woven form or in a bat form. Regardless of which configuration is employed, it has been found that by using cotton, a continuous supply of the air freshening/deodorizing composition is maintained and effective and efficient dispensing of the composition is realized. In this way, the dispensing system of the present invention achieves a continuous, trouble-free, reliable air freshening and/or deodorizing of the desired ambient area.

If desired, other suitable materials can be employed for the wicking means as a substitute for the preferred cotton material. However, any other such substitute materials should possess similar absorbency and dispersion characteristics in order to provide the desired retention of the fragrance as well as the dispensing of the fragrance when desired.

In addition, the wicking means and fragrance can be constructed in a solid form or in a gel form in order to eliminate the need for a combined wicking means and fragrance composition. Although the use of the wicking means with the liquid fragrance is preferred, these alternate constructions can be employed without departing from the scope of the present invention.

Another feature of the present invention is the attainment of a unique composition for the fragrance solution. In the present invention, a fixative is employed with the fragrance to control the rate of dispersion of the fragrance. In this way, a longer lasting air freshener/deodorizer dispensing system is attained.

By employing this preferred construction, a dispensing system is realized which overcomes all of the prior art difficulties and provides a long-lasting, reliable air freshening and/or deodorizing delivery system. In particular, it has been found that the present invention is uniquely adapted for use in commercial as well as residential environments. In this regard, the present invention is applicable for being placed in air conditioning ducts in commercial installations for delivering air freshening and/or deodorizing to an entire building or wing to which air flow through a duct is being directed. Furthermore, due to the unique combination of elements attained by the present invention, this delivery system is able to be used in direct association with all types of heat delivering systems, as well as air conditioning and air flow systems.

In this regard, it has been found that the delivery system of the present invention is uniquely applicable to use in convalescent homes, hospitals, etc., where difficulty in delivering a continuous air freshening and/or deodorizing composition has existed. However, by merely placing the present invention in an air conditioning duct or other air supply chamber, the desired air freshening and/or deodorizing fragrances are efficiently and effectively delivered throughout the desired building or zone.

It has also been found that by employing the unique wicking means, air freshening/deodorizing composition and multi-layered compact, flexible construction, the delivery system of the present invention can be easily positioned and effectively used in direct association with any conventional heating system in order to attain substantially improved fragrance dispersion. In addition, the dispensing system can be effectively positioned in otherwise inaccessible spaces or locations. These two assets are particularly employed by such locations as conventional heating systems such as hot water, electric, and hot air based systems.

Typically, a hot water based system employs radiators or hot water pipes which run along a wall directly adjacent a floor and wall. The hot water pipes are peripherally surrounded by a plurality of baffles or fins, with the fins covered by a metal housing. The heat from the hot water passes through the pipe to the radiator or fins and is conducted, by convection, through the radiator or housing to the room. By employing the present invention, the air freshening/deodorizing delivery system can be positioned in any desired location directly on or adjacent the radiator, the fins, or on the housing therefor to enable the deodorizing and/or air freshening fragrances to be carried with the warm air into the room. Electric heat systems employ similarly constructed fin and housing systems with which the dispensing system of the present invention can be easily employed to obtain the same efficacious results.

Furthermore, heated air and convection currents are employed by wood stoves to heat rooms, with the wood stoves typically having baffle means. With the present invention, the delivery system can be placed near a wood stove or on the baffles associated with the stove to attain the desired result. Care need be exercised to avoid the placement of the delivery system on a hot surface whose temperature would adversely affect the dispensing system.

Finally, hot air systems use ducts, conduits, and registers for controlling the flow of the hot air to heat the room or zones. In employing the present invention, the delivery system can be placed in the duct or register through which the hot air flows in order to heat the dispenser system and drive the dispersion of the fragrance into the room or zone. As a result, a substantially improved fragrance delivery is obtained, without requiring complex, expensive assemblies, such as are needed with prior art systems which are heated by being plugged into household electricity.

By providing a dispensing system which is capable of being used effectively and efficiently with all heating systems, the efficacy of the present invention is substantially enhanced. As detailed herein, the fragrance composition comprises a fixer for controlling its rate of dispersion and the container or housing of the dispensing system incorporates a plurality of intimately bonded integrally affixed layers, one of which comprises a metallic foil layer. As a result of this construction, the delivery system of the present invention is able to employ the heat produced by conventional heating systems to raise the temperature of the metal foil of the container. With this elevated temperature directly effecting the supply of the air freshening/deodorizing composition, the volatility of the composition is enhanced and a more effective delivery of the composition to the environment is realized.

In the preferred embodiment, the flexible container of the present invention is formed from two separate and independent sheets, each sheet of which is identical to the other and comprises a plurality of layers integrally bonded together to form the continuous sheet. Preferably, five separate layers are integrally bonded together, at least one layer of which comprises a metal foil layer which is bonded on both surfaces thereof to a plurality of separate layers formed from one or more compounds selected from the group consisting of polyester films, low density polyethylene films, ethylene acrylic acid copolymer films, and linear low density polyethylene films.

By employing this construction, two separate and independent multi-layer composite sheets are peripherally sealed to each other, forming an interior holding zone or pouch within which the super absorbent, cotton-based wicking material is mounted along with the air freshening/deodorizing composition. Once the wicking material and air freshening/deodorizing composition are positioned in the interior holding zone, the holding zone is completely sealed, assuring secure, leak free retention of the air freshening/deodorizing composition in the multi-layered container.

By employing the multi-layered construction for each of the surfaces forming the sealed container, assurance is provided that the concentrated air freshener/deodorizing composition is incapable of permeating or diffusing through the wall of the container. This assures long-term storage of the air freshening/deodorizing dispensing system of the present invention. In this way, the present invention can be retained for as long as desired and, once opened, the user is assured that the concentrated air freshening/deodorizing composition contained therein has maintained its potency and is ready for providing the desired air freshening or deodorizing results.

In a further alternate embodiment of the present invention, the air freshening/deodorizing dispensing system of the present invention also incorporates at least one permeable membrane layer positioned between the fragrance bearing wicking means and one of the multi-layered composite sheets forming the dispensing system. If desired, two separate and independent layers of a permeable membrane can be employed with the permeable membrane layers being positioned on both sides of the fragrance bearing wicking means.

By employing one or more layers of a permeable membrane positioned between the wicking means and the multi-layered composite sheet forming the air freshening/deodorizing dispensing system of the present invention, the rate of diffusion of the fragrance from the dispensing system to the ambient air can be controlled with greater precision and uniformity. By employing a permeable membrane having a porosity specifically selected for the molecular sizes of the fragrances being dispensed, the rate of diffusion of the fragrance through the permeable membrane into the ambient air can be controlled to further enhance and increase the longevity of the dispensing system of the present invention.

In this way, any desired concentration level of the air freshening/deodorizing composition can be employed regardless of the potency of the fragrance, with the dispensing system being able to completely control the dispersion rate of the fragrance from the wicking material to the ambient air in a reliable, automatic, and completely repeatable manner. In addition to providing an inherently reliable product, the air freshening/deodorizing dispensing system of the present invention may be specially constructed for any particular application or method of use. Prior to the present invention, no such specially designed dispensing system was attainable.

The invention accordingly comprises the features of construction, combinations of elements and arrangements of parts which will be exemplified in the construction hereinafter set forth and the scope of the invention will be indicated in the claims.

THE DRAWINGS

For a fuller understanding of the nature and objects of the present invention, reference should be had to the following detailed description taken in connection with the accompanying drawings, in which.

DETAILED DESCRIPTION

Figure 1:
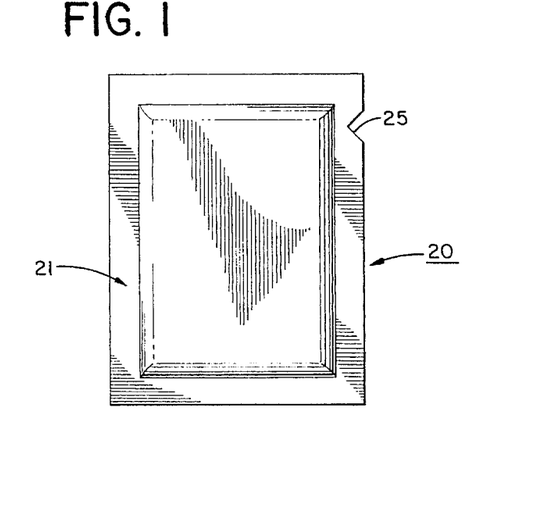
FIG. 1 is a front elevation view showing the air freshener/deodorizer dispensing system of the present invention.
Figure 2:
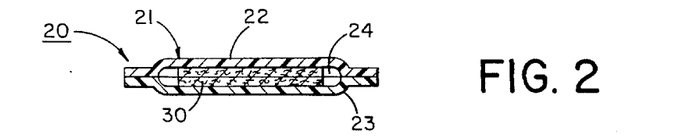
FIG. 2 is a cross-sectional side elevation view of the air freshener/deodorizer dispensing system of the present invention.

In FIGS. 1 and 2, the preferred embodiment of the air freshener/deodorizer dispensing system 20 of the present invention is clearly depicted. As shown therein, air freshener/deodorizer dispensing system 20 comprises a small, compact, flexible housing or container 21 which is formed by securely affixing side walls or panels 22 and 23 to each other.

In the preferred embodiment, as fully detailed below, side walls or panels 22 and 23 each comprise a plurality of integrally bonded layers to form a high strength, non-permeable and completely flexible panel or side wall member. In order to form container or housing 21, side walls or panels 22 and 23 are placed in overlying contacting engagement with each other and intimately bonded together about their outer peripheral edges. In this way, a completely sealed, impervious container or housing 21 is formed which is sealed about all four sides thereof and incorporates an interior holding zone or pouch 24.

In the preferred construction, in order to attain access to interior holding zone or pouch 24 of container or housing 21, a notch or slit 25 is formed along one edge of container 21. In this regard, care must be exercised to prevent notch 25 from extending inwardly from the side edge so as to extend into holding zone or pouch 24. In this way, holding zone or pouch 24 is completely sealed from the ambient surrounding. However, any individual, wishing to open holding zone or pouch 24, is capable of doing so, whenever desired, by merely applying a tearing force to notch 25, causing notch 25 to extend into holding zone or pouch 24. In this way, zone 24 is maintained completely sealed from the ambient surroundings until access to zone 24 is sought by the user.

In the preferred embodiment, prior to sealing side walls or panels 22 or 23 to each other to form container or housing 21, super absorbent, cotton-based wicking means 30 is positioned within holding zone or pouch 24. In addition, the air freshening/deodorizing composition is also placed in holding zone or pouch 24, typically in fully absorbed, dispersed, cooperating interengagement with super absorbent cotton wicking means 30. However, if wicking means 30 is fully absorbed with the air freshening/deodorizing composition and excess composition remains, the excess composition merely pools within holding zone 24, remaining in direct contact with wicking means 30. Consequently, whenever container or housing 21 is open, as detailed above, and the air freshening/deodorizing composition is dispensed, wicking means 30 is maintained fully saturated by absorbing the excess air freshening/deodorizing composition until all of the excess formulation has been fully absorbed and all of the absorbed composition has been completely dispensed.

As is apparent from FIGS. 1 and 2, as well as the foregoing detailed disclosure, air freshening/deodorizing container and dispensing system 20 of the present invention may comprise any size or shape with interior, sealed holding zone 24 also comprising any desired size, shape or configuration. However, in order to employ the teaching of the present invention, cotton wicking means 30 must be mounted within, holding zone 24 substantially filling the entire holding zone. In this way, complete absorption and distribution of all air freshening/deodorizing composition contained therein is assured.

Furthermore, wicking means 30 must also be positioned in holding zone 24 in an area which will be directly adjacent notch 25 or any other opening means incorporated with container 21. As is apparent from this disclosure, in order to attain the desired air freshening/deodorizing effect, with the composition absorbed within wicking means 30 being dispensed through the open zone, when formed, wicking means 30 must be positioned in cooperating association with the exit portal in order to assure that the desired dispensing of the air freshening/deodorizing composition to the surrounding ambient air is achieved.

In the preferred embodiment of the present invention, as discussed above, notch 25 is employed in order to open container 21 through the sealed zone thereof, to obtain access to holding zone 24 and wicking means 30. In this way, a safe, easy, and convenient opening of container and dispensing system 20 is attained. By employing notch 25, the user is capable of controlling the size of the opening being made, thereby enabling the user to form a portal through which the air freshening/deodorizing composition can exit which is directly dependant upon the amount of air freshening or deodorizing desired.

By virtually removing the entire top half of container or housing 21, maximum dispensing of the air freshener/deodorizing composition is attained. However, if the user desires a slower rate of dispensing, only a portion of the top part of container 21 would be opened, so as to prevent excessive dispersion of the air freshening/deodorizing composition from wicking means 30 through the portal formed by the user.

Figure 4:
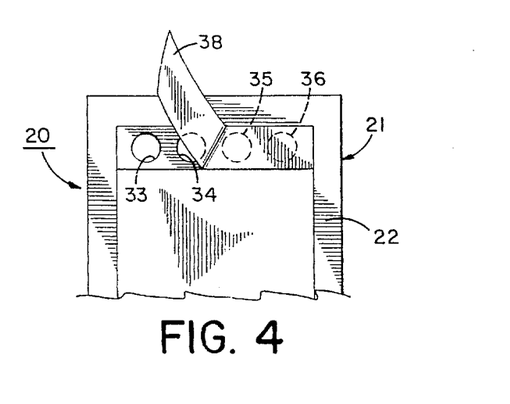
FIG. 4 is a front elevation view, partially broken away, depicting an alternate embodiment of the air freshener/deodorizer dispensing system of the present invention.

In FIG. 4, an alternate controlled opening system is disclosed wherein a plurality of holes or portals 33, 34, 35 and 36 are formed in side wall 22 of container 21. Since holes 33, 34, 35 and 36 are formed through side wall 22, these holes provide dispensing portals for enabling the air freshening/deodorizing composition to exit from holding zone 24 to the ambient surrounding. In order to prevent unwanted, early dispersion of the air freshening/deodorizing composition, prior to the user's desire, an elongated sealing strip 38 is mounted in overlying sealing interengagement with portals 33, 34, 35 and 36. In this way, holding zone 24 is completely sealed from the ambient surroundings and the desired, long-term retention of air freshening/deodorizing composition within holding zone 24 is provided.

Whenever the user is ready to employ air freshening/deodorizing container and dispensing system 20, sealing strip 38 is employed by pulling sealing strip 38 away from one or more of the portals otherwise maintained closed by sealing strip 38. As depicted in FIG. 4, sealing strip 38 is removed from portals 35 and 36, while maintaining portals 33 and 34 completely sealed. In this way, an average rate of dispersion of the air freshening/deodorizing composition is attained.

As is apparent from the foregoing disclosure, by removing sealing strip 38 from the desired number of portals, the precisely desired rate of dispersion of the air freshening/deodorizing composition is realized. If maximum distribution is desired, sealing strip 38 is completely removed. However, any other rate of dispersion can be easily attained by uncovering the desired number of portals otherwise scaled by strip 38. In this way, the consumer maintains complete control over the rate of dispersion of the air freshening/deodorizing composition while also assuring that prior to use, the air freshening/deodorizing composition is securely retained in sealed interengagement within container 21, with the composition being incapable of being dispersed or permeated through side walls or panels 22 or 23.

In the preferred embodiment, the air freshening/deodorizing composition employed in the dispensing system of the present invention comprises the uniquely constructed formulation designed specifically for providing a concentrated, potent, long-lasting air freshening and/or deodorizing effect. In accordance with the present invention, the air freshening/deodorizing composition comprises between about 90% and 99% of one or more oil-based fragrances and between about 1% and 10% by weight of a fixative for the oil-based fragrance.

In the preferred embodiment, the fixative employed in the composition of the present invention comprises methyl hydrogenated rosinate. Methyl hydrogenated rosinate is the ester of methyl alcohol and the hydrogenated mixed long chain acids derived from rosin. It has been found that this particular composition works most effectively as a fixative in providing a superior air freshening/deodorizing composition, with the preferred amount being 5% by weight.

In addition to the methyl hydrogenated rosinate, the composition of the present invention incorporates, in the preferred embodiment, a plurality of oil-based fragrances to provide the desired air freshening and/or deodorizing effect. Although a wide variety of oil-based fragrances can be employed in carrying out the present invention, without departing from the scope of the present invention, it has been found that the preferred oil-based fragrances are selected from the group consisting of fruity notes, spices, cloves, eucalyptus, floral notes, jasmine, lavenders, wintergreen, spearmint, and wood notes. By employing one or a combination of these oil-based fragrances in the preferred quantity of 95% by weight of the entire composition, the desired air freshening and/or deodorizing fragrance is attained and the desired long-lasting, air freshening/deodorizing effect is realized.

Figure 3:
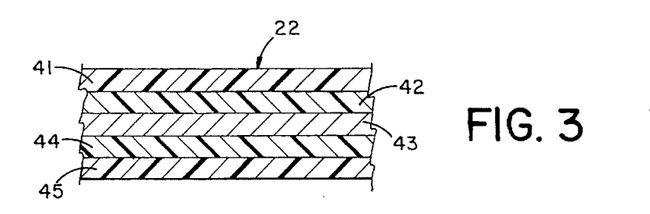
FIG. 3 is a greatly enlarged, cross-sectional elevation view, partially broken away, depicting the preferred construction of the plurality of integrally bonded layers forming the side wall of the dispensing system of the present invention.

In FIG. 3, the preferred embodiment of each of the side walls or panels 22 and 23 is depicted. Preferably, side walls or panels 22 and 23 comprise identical constructions, with both panels incorporating the identical integrally bonded multi-layered configuration. In FIG. 3, for exemplary purposes only, a portion of side wall panel 22 is shown in a greatly enlarged cross section in order to depict each of the plurality of integrally affixed layers forming side wall 22. As is apparent from the disclosure, panel 23 comprises an identical construction.

In the preferred embodiment, side wall or panel 22 and 23 comprises five separate and distinct independent layers, each of which are integrally bonded in secure, affixed interengagement to each other. The first or outer surface layer 41 comprises a polyester film, preferably having a thickness of about 48 gauge. Although other materials and thicknesses may be used for layer 41, polyester film is preferred in order to enable the surface of the layer to be printed upon.

The middle layer of side wall 22 is layer 43 which comprises a thin metal foil material. Preferably, metal foil layer 43 comprises a thickness ranging between 0.0001 and 0.0005 inches, with a thickness of 0.0003 inches being preferred.

In order to securely bond metal foil layer 43 to polyester film layer 41, layer 42 is employed. Preferably layer 42 comprises a low density polyethylene film having a thickness of about 0.00075 inches. Although other bonding films and other thicknesses may be employed, low density polyethylene is preferred and has proven to provide the desired intimate affixation of foil layer 43 to polyester layer 41.

The final two layers are layers 44 and 45. Layer 44 is similar in function to layer 42 and provides the desired secure bonding of foil layer 43 to layer 45. Although any suitable bonding film and thickness may be employed, layer 44 preferably comprises ethylene acrylic acid copolymer with a thickness of about 0.0015 inches.

Inside layer 45 of side wall 22 preferably comprises a film of linear law density polyethylene. Preferably, the thickness of layer 45 is about 0.00125 inches. The composition of layer 45 is particularly important, since the secure affixation of side wall 22 with side wall 23 is achieved by heat-sealing the outer peripheral edges of side walls 22 and 23 to each other.

In the preferred embodiment, side walls 22 and 23 are placed in overlying relationship with each other and, at the appropriate process time, the contacting surfaces of layer 45 of side walls 22 and 23 are intimately affixed together to form the desired, completely sealed container 20. By employing linear low density polyethylene film as layer 45, the desired complete sealed, bond affixation of side walls 22 and 23 is assured.

Figure 5:
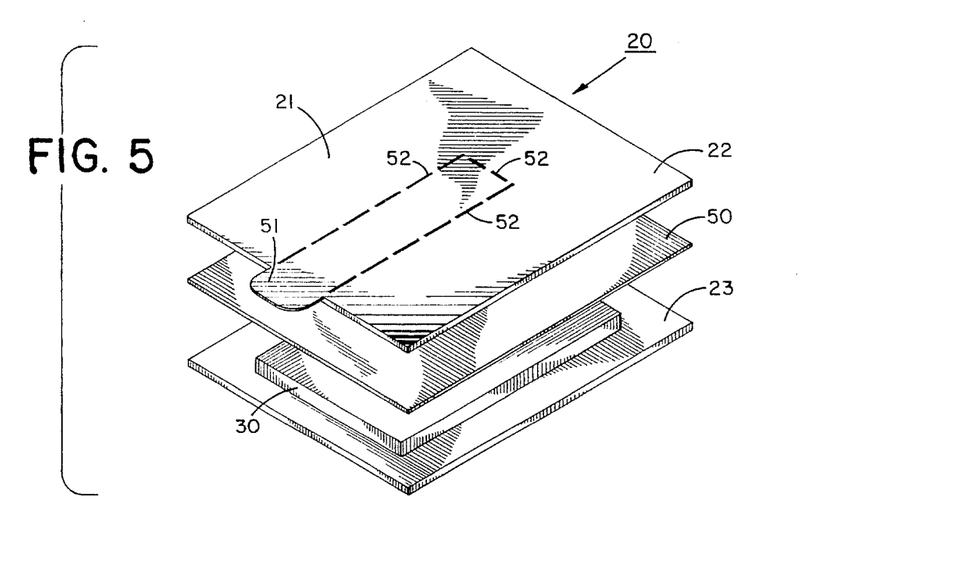
FIG. 5 is an exploded perspective view of a further alternate embodiment of the air freshener/deodorizer dispensing system of the present invention.

In FIG. 5, a further embodiment of the present invention is depicted. In this embodiment, as with the embodiments detailed above, air freshener/deodorizer dispensing system 20 comprises housing or container 21, which is formed from integrally bonded, multi-layered side walls or panels 22 and 23. In addition, this embodiment comprises wicking means 30 preferably formed from cotton material within which the desired air freshening/deodorizing composition is retained for distribution to the ambient surroundings.

In order to provide enhanced control over the rate of dispersion of the air freshening/deodorizing composition contained within wicking means 30, this embodiment of air freshener/deodorizing dispensing system 20 also incorporates a separate and independent permeable membrane layer 50 positioned between side wall 22 and wicking means 30. Preferably, permeable membrane layer 50 comprises an overall size and shape substantially equivalent to the size and shape employed tier side walls or panels 22 and 23 and is securely affixed as part of dispensing system 20 by intimately bonding the outside peripheral edge of permeable membrane layer 50 between side walls or panels 22 and 23. In this way, the desired, completely sealed container 21 is easily attained with permeable membrane layer 50 controllably positioned between side wall 22 and wicking means 30.

As with the previous embodiments, whenever the dispensing of the air freshening/deodorizing composition is desired, dispensing system 20 is opened, using any desired access means incorporated into dispensing system 20. In particular, any of the access systems detailed above can be employed, with equivalent efficacy, with the embodiment of dispensing system 20 depicted in FIG. 5.

If desired, an alternate access system can be employed as shown in FIG. 5. In this access system, a flap member 51 is formed in side wall or panel 22 by incorporating a plurality of flap-defining notches 52 in the top surface of side wall or panel 22. In the preferred construction, flap-forming notches 52 extend from the outside surface of side wall or panel 22 to metal layer 43 of side wall or panel 22, in order to assure that the interior of dispensing system 20 is sealed and the air freshening/deodorizing composition is not dispensed prematurely.

Whenever a consumer is ready to employ dispensing system 20, flap 51 is held by suitable means, such as an access tab, which enables flap 51 to separate from side wall or panel 22, revealing permeable membrane 50. Once flap 51 has been opened to the desired extent, the air freshening/deodorizing composition contained in wicking means 30 is capable of passing through the pores of permeable membrane 50 and into the surrounding ambient air.

By constructing permeable membrane 50 in the manner consistent with the molecular structure of the air freshening/deodorizing composition being employed, the rate of dispersion of the air freshening/deodorizing composition into the ambient air is precisely controlled automatically. Furthermore, the use of permeable membrane 50 assures a continuous, dependable and completely repeatable rate of dispersion of the air freshening/deodorizing composition into the ambient surroundings.

Figure 6:
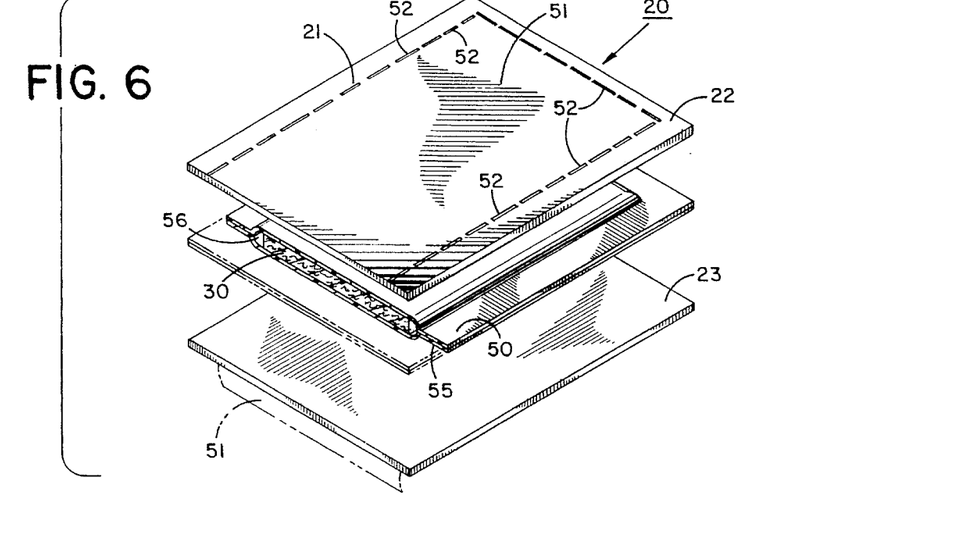
FIG. 6 is an exploded perspective view of a still further alternate embodiment of the air freshener/deodorizer dispensing system of the present invention.

As is evident from this disclosure, flap 51 may be constructed in any desired size and shape. As a result, if desired, flap 51 may be constructed with flap forming notches 52 formed in side wall or panel 22 in a manner which would substantially encompass a major portion of side wall or panel 22, as shown in FIG. 6. This enables virtually all of permeable membrane 50 to be exposed once flap 51 was opened. Although this would enable a greater quantity of the air freshening/deodorizing composition to be dispersed into the ambient surroundings, the rate of dispersion of the air freshening/deodorizing composition is still controlled by the pore size of permeable membrane 50. In this way, a continuous, substantially constant rate of dispersion is assured.

By specifically formulating permeable membrane layer 50 with a precisely desired pore size and employing particularly selected fragrances having desired molecular characteristics, the overall effectiveness and longevity of dispensing system 20 of the present invention is substantially enhanced and controlled. Furthermore, by employing permeable membrane layer 50 as part of dispensing system 20, substantially stronger concentrations of the air freshening/deodorizing composition may be employed without fear that the potency of the air freshener/deodorizer composition will be overpowering in its initial stages.

By controlling the rate of dispersion of the fragrance from the wicking means to the ambient surroundings, higher concentrated solutions of the air freshener/deodorizing composition can be employed and are efficiently and automatically dispensed, producing a continuous level of air freshening for the entire useful life of the air freshening/deodorizing composition. As a result, a highly effective and desirable dispensing system is realized.

In FIG. 6, a further alternate embodiment of the air freshening/deodorizing dispensing system 20 of the present invention is depicted. In this embodiment, dispensing system 20 incorporates a housing or container 21 formed from side walls of panels 22 and 23 in the manner detailed above. However, in order to provide a further enhanced construction, this embodiment employs permeable membrane layer 50 along with a second permeable membrane layer 55.

In the construction of this embodiment, membrane layers 50 and 55 comprise a size and shape substantially equivalent to or less than the size and shape of side walls or panels 22 and 23. If desired, membrane layers 50 and 55 are integrally affixed and secured between side walls or panels 22 and 23 as detailed above. In addition, if desired, permeable membrane layers 50 and 55 are intimately bonded to each other to form a separate and independent dispersion controlling member which comprises an internal retaining zone 56. Retaining zone 56 is employed to hold and securely retain wicking means 30. By forming a completely enclosed, independent dispersion controlling member within which wicking means 30 is securely retained, an easily assembled, dispensing system 20 is obtained which is easily employed to provide continuous dispersion of the fragrance at a fixed rate.

In accordance with the present invention, permeable membrane layers 50 and 55 may comprise any desired size and shape, provided the membrane layers are easily retained within housing or container 21 formed by side walls or panels 22 and 23. Clearly, regardless of the overall size of permeable membrane layers 50 and 55, the securement of wicking means 30 within permeable membrane layers 50 and 55 assures that all of the air freshening/deodorizing composition housed therein will be dispensed in a completely controlled manner, based upon the diffusion rate of the air freshening/deodorizing composition through the pores of permeable membrane layers 50 and 55.

In this embodiment, both side walls or panels 22 and 23 incorporate opening means formed therein to enable both sides of housing or container 21 to be opened. As depicted, enlarged flaps 51 are formed in both side walls or panels 22 and 23, to enable both side walls 22 and 23 to be opened, allowing access to both permeable membrane layers 50 and 55. As a result, greater surface area of the permeable membrane is exposed and a greater quantity of the air freshening/deodorizing composition is more readily dispensed into the ambient surroundings.

By employing this embodiment of the present invention, dispensing system 20 can be effectively employed in locations where forced air flow occurs, such as on air delivery registers or conduits. Using this embodiment, air is able to flow through dispensing system 20, continuously driving the dispersion of the desired air freshening/deodorizing composition through permeable membrane layers 50 and 55, carrying the fragrance in the air flow. As a result, the dispensing of the desired fragrance into the ambient surroundings is further enhanced and efficiently achieved.

Furthermore, in accordance with the present invention, any desired opening means can be employed in order to gain access to the permeable membrane. Although several alternate embodiments have been shown in the drawings, other constructions such as tear strips and integrally formed tear-filaments can be employed with equal efficacy. Consequently, all alternate constructions which achieve substantially the same results are encompassed within the scope of this invention.

Figure 7:
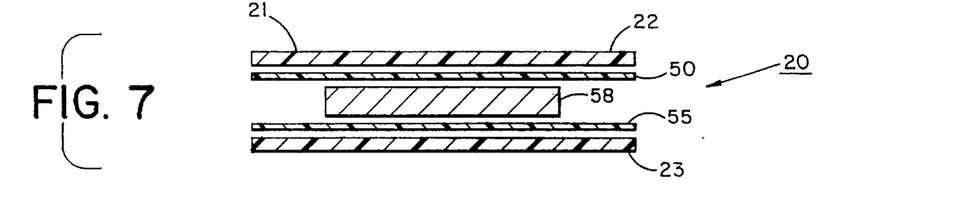
FIG. 7 is an exploded perspective view of an additional alternate embodiment of the air freshener/deodorizer dispensing system of the present invention.

In FIG. 7, a further alternate embodiment of the present invention is depicted. In this embodiment, dispensing system 20 incorporates a container or housing 21 formed from side walls or panels 22 and 23, as detailed above. In addition, two permeable membrane layers 50 and 55 are also employed in this embodiment.

As clearly depicted in FIG. 7, in this embodiment of the present invention, permeable membrane layers 50 and 55 are constructed with an overall size and shape substantially equivalent to the size and shape of side walls or panels 22 and 23, and are mounted in juxtaposed spaced relationship to each other with fragrance bearing means 58 sandwiched therebetween. When fully assembled, membrane layers 50 and 55 are integrally bonded to each other and to side walls or panels 22 and 23 about their respective outer peripheral edges, to form an integrally sealed container or housing 21 which defines dispensing system 20. In addition, any desired access means can be employed to enable the user to open dispensing system 20 and allow the fragrance retained therein to be dispensed through permeable membrane layers 50 and 55.

In addition, since two membrane layers are employed, with fragrance bearing means 58 positioned between permeable membrane layers 50 and 55, both side walls or panels 22 and 23 can both incorporate access means to enable either side or, if desired, sides of container or housing 21 to be opened for fragrance dispensing therethrough.

In this embodiment, as with the previous embodiments detailed above, any desired fragrance dispensing system can be employed. Although wicking means incorporating the desired fragrance composition, as fully detailed above, may be positioned between permeable membrane layers 50 and 55 of this embodiment, FIG. 7 depicts an alternate construction wherein a unitary fragrance holding or bearing member 58 is depicted.

As shown, fragrance bearing member 58 comprises a solid construction or a gel construction securely retained between permeable membrane layers 50 and 55. If desired, any type of fragrance bearing member may be employed in this embodiment or in any other embodiments detailed above. Regardless of the type of fragrance bearing member used, the dispersion of the desired fragrance through the side walls or panels 22 and 23 is attained.

By employing any of the embodiments shown in FIGS. 5–7, the membrane layer provides a controlled dispersion rate for the fragrance. In this way, assurance is provided that a continuous, precisely controlled level of fragrance is dispensed into the ambient surroundings, based upon the desired parameters sought by the manufacturer or the consumer.

Furthermore, permeable membrane layers 50 and 55 may be formed from any suitable material capable of providing a layer compatible with side walls or panels 22 and 23, as well as incorporating a pore size consistent with the molecular structure of the fragrance to be dispersed therethrough. Preferably, permeable membrane layers 50 and 55 are formed from polymeric plastic films or sheets which are impermeable to liquids but allow vapors to pass therethrough. Generally, any suitable polymeric film or sheet can be employed, such as sheets or films formed from polyurethane, polyethers, polyesters, polypropylenes, polystyrene, and combinations thereof.

It will thus be seen that the objects set forth above, among those made apparent from the preceding description, are efficiently attained and, since certain changes may be made in the above constructions without departing from the scope of the present invention, it is intended that all matter contained in the above description or shown in the accompanying drawings shall be interpreted as illustrative and not in a limiting sense.

It is also to be understood that the following claims are intended to cover all of the generic and specific features of the invention herein described and all statements of the scope of the invention which, as a matter of language, might be said to fall therebetween.

Particularly, it is to be understood that in said claims, ingredients or compounds recited in the singular are intended to include compatible mixtures of such ingredients wherever the sense permits.

Having described my invention, what I claim as new and desire to secure by Letters Patent is:

1. A dispensing system for providing controlled, long-term release of an air freshening and/or a deodorizing fragrance, said system comprising A. a container formed from two independent, multi-layered, flexible sheets and incorporating a sealed holding zone, each of said sheets comprising
      a. at least one barrier layer formed from metal foil for preventing transfer of the air freshening/deodorizing composition from the holding zone to the ambient surroundings when the container is sealed,
      b. at least one low density, linear polyethylene film layer intimately bonded to one surface of the barrier layer for providing inherent strength and surface sealability between the two independent multi-layered, flexible sheets, and
      c. at least one polyester layer integrally bonded to the opposed surface of the barrier metal foil layer for providing a print receiving surface;

B. a highly concentrated, long-lasting, air freshening/deodorizing composition contained within the holding zone and comprising
      a. between about 90% and 99% by weight of the entire composition of at least one oil-based fragrance, and
      b. between about 1% and 10% by weight of the entire composition of a fixative;

C. fragrance holding means mounted in the holding zone of the container and incorporating the air freshener/deodorizing composition; and D. a composition dispensing portal
      a. formed in the container in a normally sealed configuration to prevent the release of the air freshening/deodorizing composition from the holding zone until desired, and
      b. controllably openable for providing a fragrance dispensing portal, whereby the air freshening/deodorizing fragrance is able to exit from the fragrance holding means into the ambient surroundings.

2. The dispensing system defined in claim 1, wherein the fragrance holding means is further defined as comprising one selected from the group consisting of gels, solids, and liquid fragrance bearing wicking means.

3. The dispensing system defined in claim 2, wherein said fragrance holding means is further defined as being positioned in the holding zone in cooperative association with the dispensing portal for assuring ready transfer of the air freshening/deodorizing composition to the dispensing portal for dispersement into the ambient surroundings.

4. A dispensing system for providing controlled, long-term release of an air freshening and/or a deodorizing fragrance, said system comprising A. a container formed from two independent, multi-layered, flexible sheets and incorporating a sealed holding zone;

B. a highly concentrated, long-lasting, air freshening/deodorizing composition contained within the holding zone and comprising a. between about 90% and 99% by weight of the entire composition of at least one oil-based fragrance, and b. between about 1% and 10% by weight of the entire composition of a fixative;

C. fragrance holding means mounted in the holding zone of the container and incorporating the air freshener/deodorizing composition;

D. a first permeable membrane layer mounted in the container and positioned between the fragrance holding means and one of said multi-layered flexible sheets for controlling the rate of dispersion of the air-freshening/deodorizing composition;

E. a second permeable membrane layer positioned in juxtaposed spaced relationship with the first membrane layer, with the fragrance holding means sandwiched therebetween; and F. a composition dispensing portal
  a. formed in the container in a normally sealed configuration to prevent the release of the air freshening/deodorizing composition from the holding zone until desired, and
  b. controllably openable for providing a fragrance dispensing portal, whereby the air freshening/deodorizing fragrance is able to exit from the fragrance holding means into the ambient surroundings after passage through at least one permeable membrane layer.

5. The dispensing system defined in claim 4, wherein the fragrance holding means is further defined as comprising one selected from the group consisting of gels, solids, and liquid fragrance bearing wicking means.

6. The dispensing system defined in claim 5, wherein said wicking means is further defined as being constructed for providing continuous, long-term transfer of the air freshening/deodorizing composition to the ambient surroundings.

7. The dispensing system defined in claim 4, wherein said fragrance holding means is further defined as comprising highly absorbent wicking means which is in direct absorbing and wicking interengagement with the air freshener/deodorizer composition.

8. The dispensing system defined in claim 7, wherein said wicking means is further defined as being constructed for providing continuous, long-term transfer of the air freshening/deodorizing composition to the ambient surroundings.

9. The dispensing system defined in claim 7, wherein said wicking means is further defined as being formed from cotton batt.

10. The dispensing system defined in claim 7, wherein said wicking means is further defined as being formed from woven cotton material.

11. The dispensing system defined in claim 7, wherein said wicking means is further defined as being sized for substantially filling the holding zone and retaining the air freshening/deodorizing composition fully absorbed therein.

12. The dispensing system defined in claim 4, wherein said first and second membrane layers are further defined as being bonded together about their outer peripheral surfaces, thereby establishing a retaining zone for sealingly securing the fragrance holding means.

13. The dispensing system defined in claim 4, wherein said permeable membrane is further defined as being formed from a polymeric plastic sheet.

14. The dispensing system defined in claim 13, wherein said polymeric plastic sheet is further defined as comprising one selected from the group consisting of polyurethanes, polyethers, polyesters, polypropylenes, polystyrene, and combinations thereof.

15. The dispensing system defined in claim 4, wherein each of said multi-layered flexible sheets forming said container is further defined as comprising
  a. at least one barrier layer formed from metal foil for preventing transfer of the air freshening/deodorizing composition from the holding zone to ambient surroundings when the container is sealed,
  b. at least one low density, linear polyethylene film layer intimately bonded to one surface of at least one barrier layer for providing inherent strength and surface sealability between the two independent multi-layered, flexible sheets, and
  c. at least one polyester layer integrally bonded to the opposed surface of at least one barrier metal foil layer for providing a print receiving surface.

16. A dispensing system for providing controlled, long-term release of an air freshening and/or a deodorizing fragrance, said system comprising
  A. a container formed from two independent, multi-layered, flexible sheets and incorporating a sealed holding zone, each of said multi-layered, flexible sheets being further defined as comprising
    a. at least one barrier layer formed from metal foil for preventing transfer of the air freshening/deodorizing composition from the holding zone to the ambient surroundings when the container is sealed,
    b. at least one low density, linear polyethylene film layer intimately bonded to one surface of the barrier layer for providing inherent strength and surface sealability between the two independent multi-layered, flexible sheets, and
    c. at least one polyester layer integrally bonded to the opposed surface of the barrier metal foil layer for providing a print receiving surface;
  B. a highly concentrated, long-lasting, air freshening/deodorizing composition contained within the holding zone and comprising
    a. between about 90% and 99% by weight of the entire composition of at least one oil-based fragrance selected from the group consisting of fruity notes, spices, cloves, eucalyptus, floral notes, jasmine, lavender, wintergreen, spearmint, and wood notes, and
    b. between about 1% and 10% by weight of the entire composition of a fixative comprising methyl hydrogenated rosinate;
  C. highly absorbent wicking means
    a. mounted in the holding zone of the container in direct, absorbing and wicking interengagement with the air freshener/deodorizing composition;
    b. positioned in the holding zone in cooperative association with a dispensing portal for assuring ready transfer of the air freshening/deodorizing composition to the dispensing portal for dispersement into the ambient surroundings; and
    c. constructed for providing continuous, long-term transfer of the air freshening/deodorizing composition;
  D. at least one permeable membrane layer positioned between the wicking means and one of said multi-layered flexible sheets for controlling the rate of dispersion of the air freshener/deodorizer composition; and
  E. a composition dispensing portal
    a. formed in the container in a normally sealed configuration to prevent the release of the air freshening/deodorizing composition from the holding zone until desired, and b. controllably openable for providing a fragrance dispensing portal, whereby the air freshening/deodorizing fragrance is able to exit from the wicking means into the ambient surroundings after passage through the permeable membrane layer.

17. A dispensing system for providing controlled, long-term release of an air freshening and/or a deodorizing fragrance, said system comprising A. a container formed from two independent, multi-layered, flexible sheets and incorporating a sealed holding zone each of said sheets comprising;
 a. at least one barrier layer formed from metal foil for preventing transfer of the air freshening/deodorizing composition from the holding zone to the ambient surroundings when the container is sealed,
 b. at least one low density, linear polyethylene film layer intimately bonded to one surface of the barrier layer for providing inherent strength and surface sealability between the two independent multi-layered, flexible sheets, and
 c. at least one polyester layer integrally bonded to the opposed surface of the barrier metal foil layer for providing a print receiving surface;

B. a highly concentrated, long-lasting, air freshening/deodorizing composition contained within the holding zone and comprising
 a. between about 90% and 99% by weight of the entire composition of at least one oil-based fragrance, and
 b. between about 1% and 10% by weight of the entire composition of a fixative;

C. fragrance holding means mounted in the holding zone of the container and incorporating the air freshener/deodorizing composition;

D. a first permeable membrane layer mounted in the container and positioned between the fragrance holding means and one of said multi-layered flexible sheets for controlling the rate of dispersion of the air-freshening/deodorizing composition; and E. a composition dispensing portal
 a. formed in the container in a normally sealed configuration to prevent the release of the air freshening/deodorizing composition from the holding zone until desired, and
 b. controllably openable for providing a fragrance dispensing portal, whereby the air freshening/deodorizing fragrance is able to exit from the fragrance holding means into the ambient surroundings.

* * * * *